US009271729B2

(12) United States Patent
Nicholson, IV

(10) Patent No.: US 9,271,729 B2
(45) Date of Patent: Mar. 1, 2016

(54) SYSTEM OF FASTENING GASTRIC SLEEVES

(76) Inventor: William D. Nicholson, IV, Dallas, TX (US)

(*) Notice: Subject to any disclaimer, the term of this patent is extended or adjusted under 35 U.S.C. 154(b) by 625 days.

(21) Appl. No.: 13/427,444

(22) Filed: Mar. 22, 2012

(65) Prior Publication Data
US 2012/0245605 A1 Sep. 27, 2012

Related U.S. Application Data

(60) Provisional application No. 61/466,130, filed on Mar. 22, 2011.

(51) Int. Cl.
A61B 17/04 (2006.01)
A61B 17/12 (2006.01)
A61B 17/08 (2006.01)
A61B 17/10 (2006.01)
A61B 17/00 (2006.01)
A61B 17/29 (2006.01)

(52) U.S. Cl.
CPC ............... *A61B 17/08* (2013.01); *A61B 17/10* (2013.01); *A61B 2017/00818* (2013.01); *A61B 2017/2905* (2013.01)

(58) Field of Classification Search
CPC ............... A61B 17/08; A61B 17/10; A61B 2017/00818; A61B 2017/2905
USPC ......... 606/142, 151, 139, 140, 141, 143, 157, 606/213, 214, 215
See application file for complete search history.

(56) References Cited

U.S. PATENT DOCUMENTS

| 3,867,944 | A | * | 2/1975 | Samuels | 606/158 |
| 5,242,456 | A | * | 9/1993 | Nash et al. | 606/142 |
| 5,620,452 | A | | 4/1997 | Yoon | |
| 2004/0097989 | A1 | | 5/2004 | Molina Trigueros | |
| 2006/0235469 | A1 | * | 10/2006 | Viola | 606/219 |
| 2007/0118163 | A1 | | 5/2007 | Boudreaux et al. | |
| 2008/0319456 | A1 | * | 12/2008 | Hart | 606/142 |

(Continued)

FOREIGN PATENT DOCUMENTS

WO 9841154 A1 9/1998

OTHER PUBLICATIONS

PCT International Search Report and Written Opinion of the International Searching Authority for related PCT/US2012/30154, dated Dec. 7, 2012, 9 pages.

(Continued)

*Primary Examiner* — Katrina Stransky
(74) *Attorney, Agent, or Firm* — Elizabeth Philip Dahm; Kelly J. Kubasta; Ferguson, Braswell & Fraser

(57) ABSTRACT

A surgical clip comprising a curved backbone having a lower side, a plurality of arms coupled to the curved backbone and extending therefrom in the same direction, each arm having a facing side, and an interior surface comprising the lower side of the curved backbone and the facing sides of the plurality of arms. A method of installing a surgical clip comprising fastening body tissue with surgical staples to form a stapled edge, and fastening the surgical clip across the stapled edge to inhibit the development of openings along the stapled edge. A tool for installing a surgical clip, the tool comprising a clip delivery end to carry and position the surgical clip, and an actuator to cause the surgical clip to engage and secure the stapled edge of body tissue.

16 Claims, 6 Drawing Sheets

(56) References Cited

U.S. PATENT DOCUMENTS

2009/0065551 A1* 3/2009 Green et al. ............... 227/176.1
2010/0204728 A1* 8/2010 Bettuchi ...................... 606/213

OTHER PUBLICATIONS

PCT International Preliminary Report on Patentability for related PCT/US2012/30154, dated Oct. 3, 2013, 8 pages.

* cited by examiner

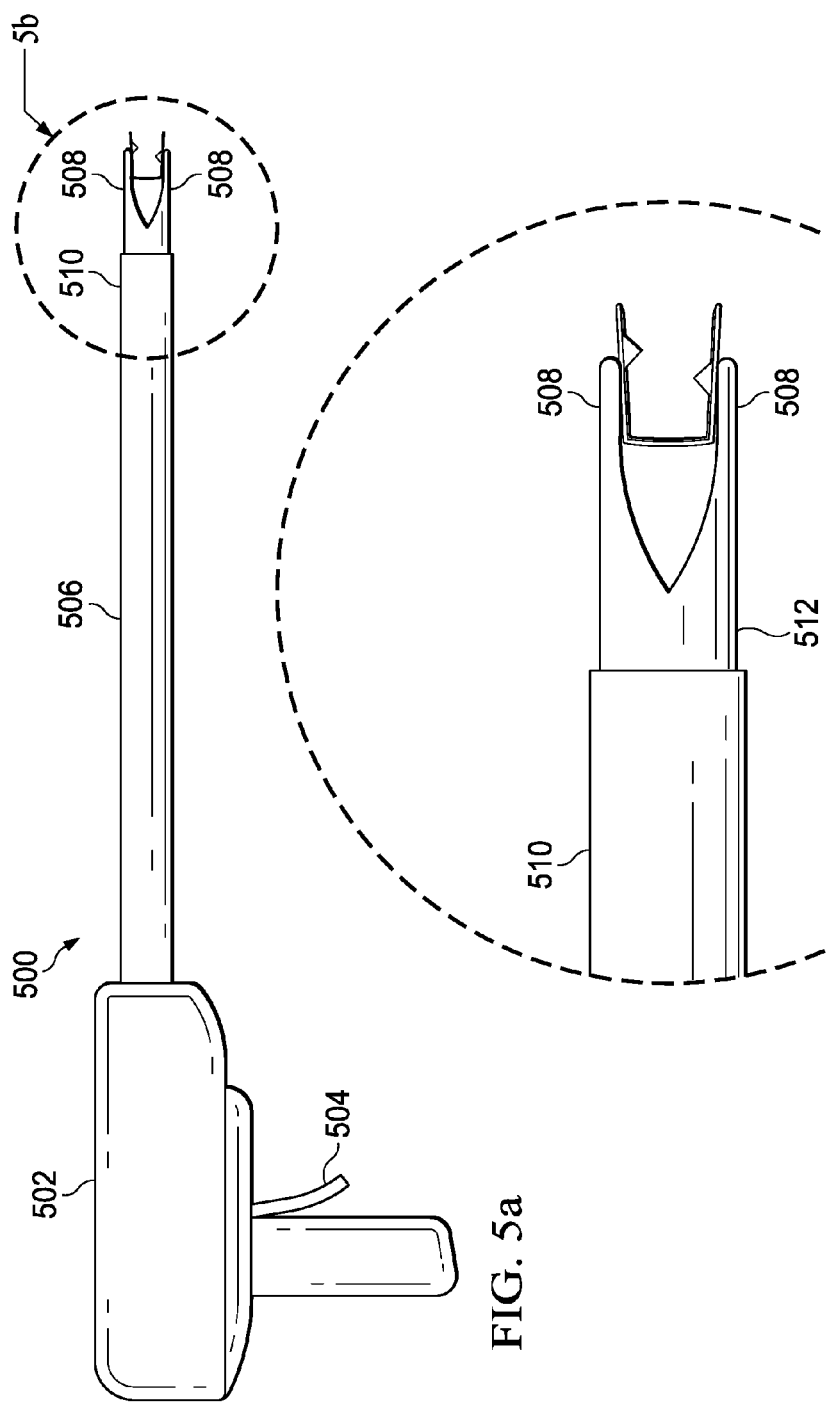

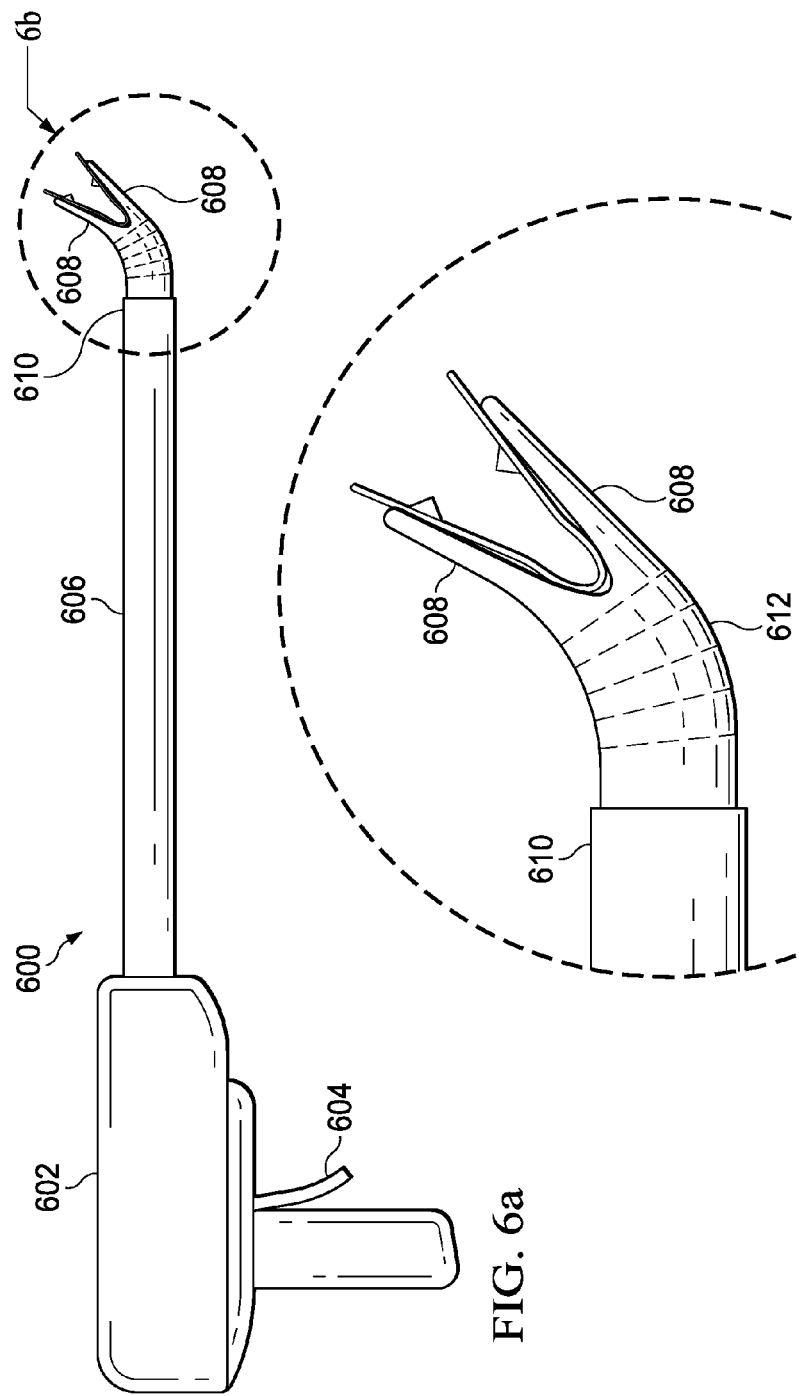

SYSTEM OF FASTENING GASTRIC SLEEVES

CROSS REFERENCE TO RELATED APPLICATIONS

The present application claims the benefit under 35 U.S.C. §119(e) of U.S. Provisional Patent Application Ser. No. 61/466,130 filed Mar. 22, 2011 and entitled "System of Fastening Gastric Sleeves," which is incorporated herein by reference for all purposes.

TECHNICAL FIELD

The present disclosure relates generally to systems and methods of fastening a gastric sleeve to substantially prevent leakage of gastric fluid into the abdominal cavity, and more particularly, to a surgical clip that inhibits the development of holes and gaps along a stapled edge of a gastric sleeve.

BACKGROUND

During gastric sleeve surgery (sleeve gastrectomy), a portion of the stomach is removed, and the open edges of the stomach tissue are then attached together using multiple rows of surgical staples to form a gastric sleeve. After surgery, and as the body moves, holes or gaps may develop along the stapled edge of the gastric sleeve, thereby allowing gastric fluid to leak into the abdominal cavity, which can lead to life threatening complications. Bacteria from gastric contents can cause a severe infection in the abdominal cavity that may result in sepsis or septic shock, which can eventually lead to multiple organ failure and even death.

SUMMARY

Embodiments of the present disclosure generally provide systems and methods for fastening a gastric sleeve to inhibit the development of holes or gaps along the stapled edge of the gastric sleeve and thereby substantially prevent leakage of gastric fluid into the abdominal cavity.

In an embodiment, the present disclosure provides a surgical clip comprising a curved backbone having a length and a width, and two arms each having a depth. The surgical clip may comprise one or more grippable prong components. The surgical clip may further comprise reinforced adhesive material disposed on an interior surface thereof. In an embodiment, the surgical clip is crimpable. In another embodiment, the surgical clip is a spring memory clip.

In another embodiment, the present disclosure provides a surgical clip comprising a curved backbone having a lower side, a plurality of arms coupled to the curved backbone and extending therefrom in the same direction, each arm having a facing side, and an interior surface comprising the lower side of the curved backbone and the facing sides of the plurality of arms. The surgical clip may further comprise a plurality of grippable prongs disposed along the interior surface. The surgical clip may further comprise reinforced adhesive material disposed along the interior surface. In an embodiment, the surgical clip is crimpable to engage and secure body tissue. In another embodiment, each of the plurality of arms of the surgical clip is spring loaded and biased in a closed position.

In an embodiment, the present disclosure provides a method for fastening a gastric sleeve comprising installing a surgical clip along a length of the stapled edge of the gastric sleeve to reinforce the closure formed by the stapled edge.

In another embodiment, the present disclosure provides a method for fastening a gastric sleeve comprising installing a surgical clip across one or more rows of staples along a depth of the stapled edge of the gastric sleeve.

In another embodiment, the present disclosure provides a method for installing a surgical clip comprising disposing the surgical clip in a disengaged position over open edges of stomach tissue along the stapled edge of the gastric sleeve and closing the surgical clip around the open edges of stomach tissue into engagement with the stapled edge of the gastric sleeve. In an embodiment, closing the surgical clip comprises crimping the surgical clip. In another embodiment, closing the surgical clip comprises releasing a spring memory clip.

In another embodiment, the present disclosure provides a method of installing a surgical clip comprising fastening body tissue with surgical staples to form a stapled edge, and fastening the surgical clip across the stapled edge to inhibit the development of openings along the stapled edge. The method may further comprise positioning the curved backbone around open edges of body tissue along the stapled edge before fastening the surgical clip across the stapled edge. The method may further comprise extending the plurality of arms over one or more rows of surgical staples forming the stapled edge before fastening the surgical clip across the stapled edge. In an embodiment, the method further comprises gripping the body tissue forming the stapled edge with grippable prongs disposed along an interior surface of the surgical clip. The method may further comprise adhering the surgical clip to the stapled edge.

In another embodiment, the present disclosure provides a method of installing a surgical clip comprising positioning the surgical clip along a stapled edge of body tissue, engaging the stapled edge of body tissue with the plurality of arms, and crimping the surgical clip to secure the stapled edge of body tissue. The method may further comprise gripping the body tissue forming the stapled edge with grippable prongs disposed along an interior surface of the surgical clip.

In another embodiment, the present disclosure provides a method of installing a surgical clip comprising forcing open the spring loaded arms of the surgical clip, positioning the surgical clip along a stapled edge of body tissue, and releasing the spring loaded arms to engage and secure the stapled edge of body tissue. The method may further comprise gripping the body tissue forming the stapled edge with grippable prongs disposed along an interior surface of the surgical clip.

In an embodiment, the present disclosure provides a surgical clip applier for installing the surgical clip to the gastric sleeve. In an embodiment, the surgical clip applier comprises a clip delivery end with a stationary axis. In another embodiment, the surgical clip applier comprises a clip delivery end with a rotatable axis.

In another embodiment, the present disclosure provides a tool for installing a surgical clip comprising a clip delivery end to carry and position the surgical clip; and an actuator to cause the surgical clip to engage and secure the stapled edge of body tissue. In an embodiment, the actuator causes the clip to be crimped. In another embodiment, the actuator releases the clip to a closed position. The tool may further comprise a handle, a trocar coupled to the handle and coupled to the clip delivery end, and jaws coupled to the clip delivery end, wherein a plurality of surgical clips are loaded through the handle into the trocar, and a surgical clip is conveyed through the clip delivery end to the jaws. In an embodiment, the clip delivery end has a stationary axis. In another embodiment, the clip delivery end has a rotatable axis.

BRIEF DESCRIPTION OF THE DRAWINGS

For a more complete understanding of the present disclosure and its features, reference is now made to the following description, taken in conjunction with the accompanying drawings, in which:

FIG. 5a is an exemplary illustration of a surgical clip applier used to install the surgical clip of FIG. 1 in accordance with one embodiment of the present disclosure;

FIG. 5b is an enlarged illustration of the clip delivery end of the surgical clip applier of FIG. 5a, the clip delivery end having a stationary axis in accordance with one embodiment of the present disclosure;

FIG. 6a is an exemplary illustration of a surgical clip applier used to install the surgical clips of FIG. 1 in accordance with one embodiment of the present disclosure; and FIG. 6b is an enlarged illustration of the clip delivery end of the surgical clip applier of FIG. 6a, the clip delivery end having a rotatable axis in accordance with one embodiment of the present disclosure.

DETAILED DESCRIPTION

The present disclosure generally provides systems and methods for fastening gastric sleeves to inhibit the development of holes or gaps along the stapled edge of the gastric sleeve.

Figure 1:
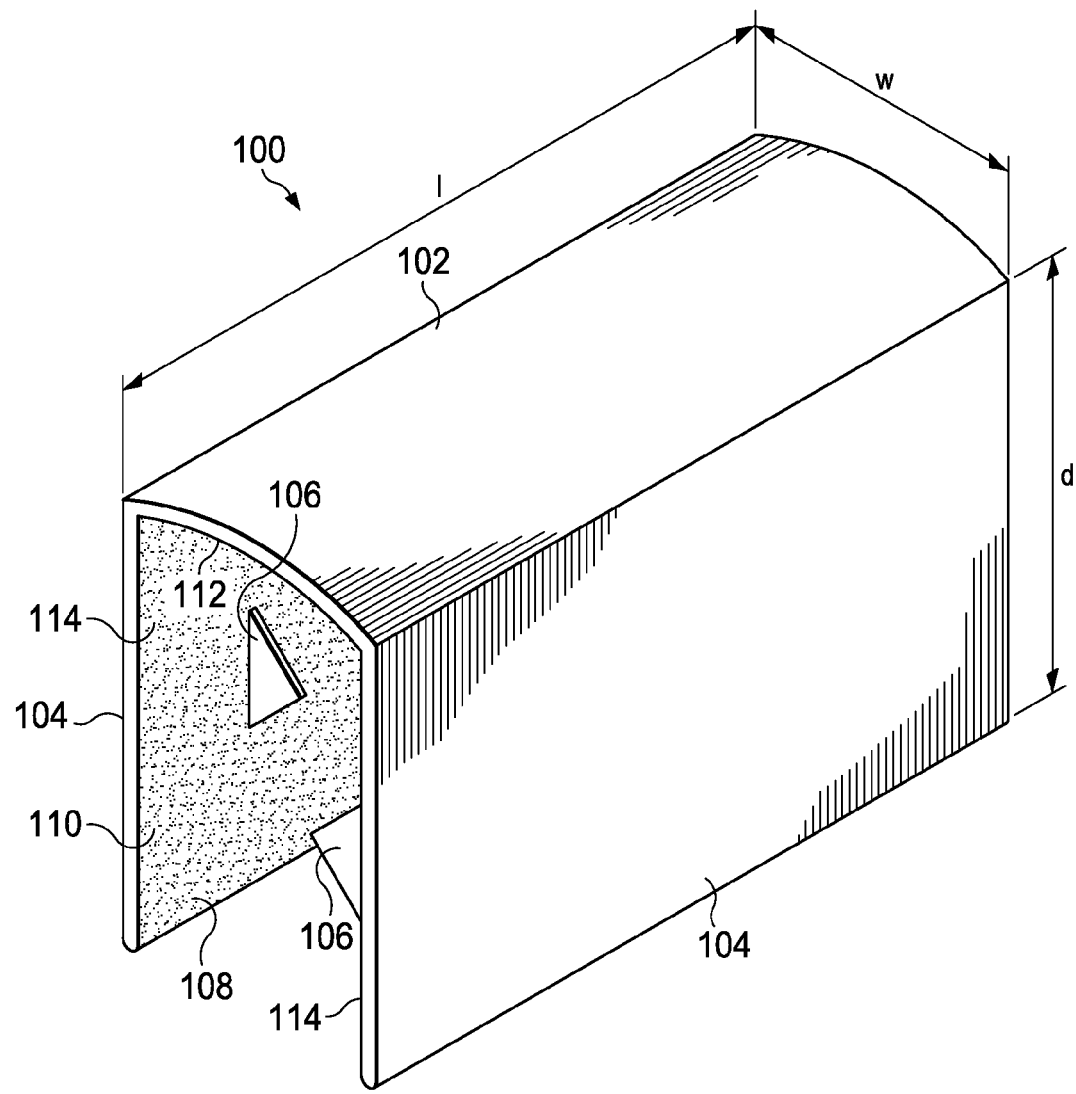
FIG. 1 is an exemplary illustration of a crimpable surgical clip in accordance with one embodiment of the present disclosure.

FIG. 1 illustrates a gastric sleeve fastening system comprising a crimpable surgical clip 100 according to an embodiment of the present disclosure. It should be understood that the crimpable surgical clip 100 shown in FIG. 1 is for illustrative purposes only and that any other suitable system or subsystem could be used in conjunction with, or in lieu of, crimpable surgical clip 100 according to one embodiment of the present disclosure.

According to an embodiment of the present disclosure, crimpable surgical clip 100 may comprise a curved backbone 102 and two arms 104 connected thereto. The interconnection between the curved backbone 102 and the two arms 104 may be generally square-shaped, with each of the two arms 104 extending generally perpendicular to the curved backbone 102 as shown in FIG. 1. In other embodiments, the interconnection between the curved backbone 102 and the two arms 104 may be generally rounded and/or semi-circular in shape.

An interior surface 110 of the crimpable surgical clip 100 comprises the lower side 112 of the curved backbone 102 and the facing sides 114 of each of the arms 104. In an embodiment, grippable prongs 106 may be provided along the interior surface 110 of the crimpable surgical clip 100. Optionally, a layer of reinforced adhesive material 108 may also be disposed along the interior surface 110 of the crimpable surgical clip 100.

In an embodiment, curved backbone 102 may have a width (w) measuring about 4 mm when in the open or disengaged position and a length (l) measuring about 1 cm. In an embodiment, each arm 104 may have a depth (d) measuring about 6 mm and a length (l) substantially the same as the curved backbone 102.

In an embodiment, one or more of curved backbone 102, arms 104, and grippable prongs 106 of the crimpable surgical clip 100 may be made of titanium, another suitable biocompatible medical grade material, or any combination thereof.

In an embodiment, reinforced adhesive material 108 may be employed to adhere the crimpable surgical clip 100 to the stomach tissue forming the gastric sleeve. Reinforced adhesive material 108 may be made of any suitable biocompatible medical grade adhesive material.

In operation, as described in more detail below, crimpable surgical clip 100 may be installed to fasten the open edges of stomach tissue along the stapled edge of the gastric sleeve according to one embodiment of the present disclosure. In particular, crimpable surgical clip 100 may be crimped such that the arms 104 engage the stomach tissue forming the stapled edge of the gastric sleeve. Grippable prongs 106 and reinforced adhesive material 108 may optionally be provided to further secure crimpable surgical clip 100 to the gastric sleeve and thereby inhibit the development of holes or gaps in the stapled edge of the gastric sleeve according to one embodiment of the present disclosure.

Figure 2:
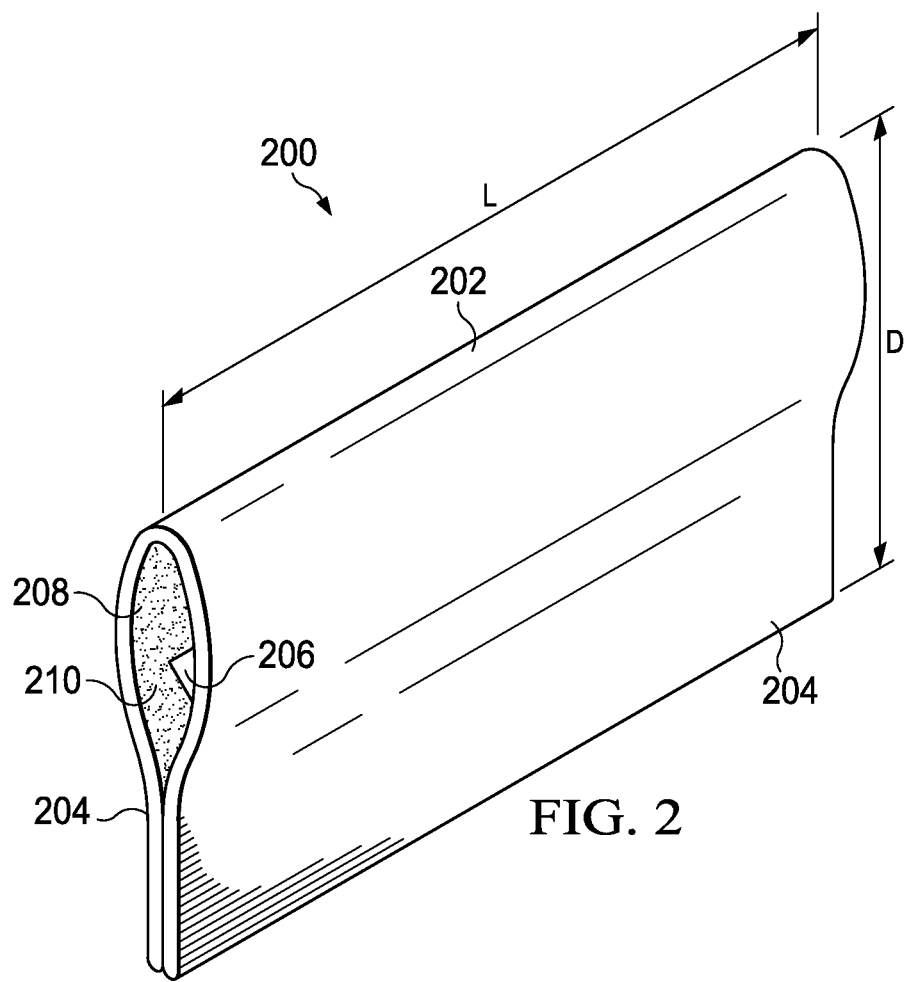
FIG. 2 is an exemplary illustration of a spring memory surgical clip in accordance with one embodiment of the present disclosure.

FIG. 2 generally illustrates another embodiment of a gastric sleeve fastening system comprising a spring memory surgical clip 200. It should be understood that the spring memory surgical clip 200 shown in FIG. 2 is for illustrative purposes only and that any other suitable system or subsystem could be used in conjunction with or in lieu of spring memory surgical clip 200 according to one embodiment of the present disclosure.

In one embodiment, spring memory surgical clip 200 could generally be similar to crimpable surgical clip 100 shown in and described in conjunction with FIG. 1 above (with like parts having similar numbers). As such, spring memory surgical clip 200 may comprise a curved backbone 202, two arms 204 connected thereto, and an interior surface 210. In contrast to the arms 104 of crimpable surgical clip 100, the arms 204 of clip 200 are spring-loaded and biased to a closed, engaging position as depicted in FIG. 2. In an embodiment, grippable prongs 206 may be provided along the interior surface 210 of the spring memory surgical clip 200. Optionally, a layer of reinforced adhesive material 208 may also be disposed along the interior surface 210 of the spring memory surgical clip 200.

In an embodiment, curved backbone 202 may have a length (L) measuring about 1 cm. Each arm 104 may have a depth (D) measuring about 6 mm and a length (L) substantially the same as the curved backbone 202.

In an embodiment, one or more of curved backbone 202, arms 204, and grippable prongs 206 of the spring memory surgical clip 200 may be made of titanium, another suitable biocompatible medical grade material, or any combination thereof.

In an embodiment, reinforced adhesive material 208 may be employed to adhere the spring memory surgical clip 200 to the stomach tissue forming the gastric sleeve. Reinforced adhesive material 208 may be made of any suitable biocompatible medical grade adhesive material.

In operation, as described in more detail below, spring memory surgical clip 200 may be installed to fasten the open edges of stomach tissue along the stapled edge of the gastric sleeve according to one embodiment of the present disclosure. In particular, the arms 204 of spring memory surgical clip 200 may be forced open for positioning with respect to the open edges of stomach tissue along the stapled edge and then released such that the arms 204 engage the stomach tissue forming the stapled edge of the gastric sleeve. Grippable prongs 206 and reinforced adhesive material 208 may optionally be provided to further secure spring memory surgical clip 200 to the gastric sleeve and thereby inhibit the development of holes or gaps in the stapled edge of the gastric sleeve according to one embodiment of the present disclosure.

Figure 3A:
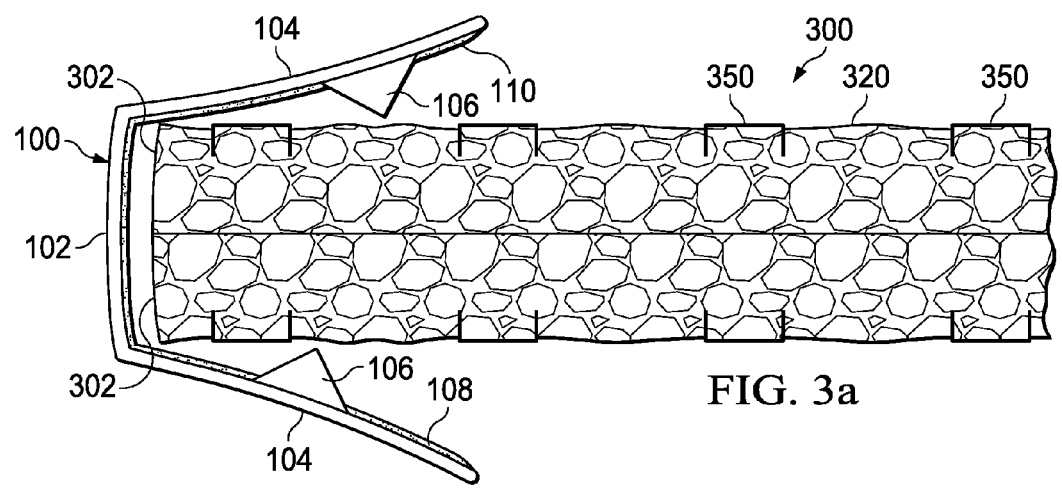
FIG. 3a is a side view of the surgical clip of FIG. 1 in a disengaged position while being positioned over open edges of stomach tissue along the stapled edge of the gastric sleeve in accordance with one embodiment of the present disclosure.

FIG. 3a depicts a side view of the crimpable surgical clip 100 of FIG. 1 in a disengaged position while being oriented for installation along a stapled edge 320 of a gastric sleeve 300 to fasten open edges 302 of stomach tissue together in accordance with one embodiment of the present disclosure. As depicted, the stapled edge 320 comprises a plurality of rows of staples 350 that form a closure for the gastric sleeve 300 while open edges 302 of stomach tissue remain. As depicted in FIG. 3a, curved backbone 102 may be positioned around the open edges 302 of remaining stomach tissue such that the arms 104 extend over one or more rows of surgical staples 350.

Figure 3B:
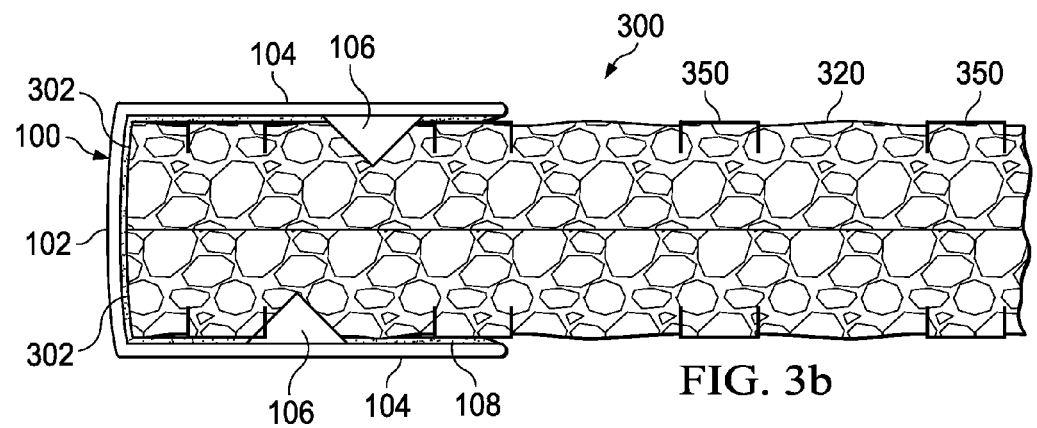
FIG. 3b is a side view of the surgical clip of FIG. 1 in an engaged or crimped position to fasten the open edges of stomach tissue together in accordance with one embodiment of the present disclosure.

FIG. 3b depicts a side view of the crimpable surgical clip 100 of FIG. 1 in the engaged or crimped position around the open edges 302 of stomach tissue, with the arms 104 extending across several rows of surgical staples 350 of the stapled edge 320 of gastric sleeve 300 in accordance with one embodiment of the present disclosure. In this configuration, the grippable prongs 106 may extend into the stomach tissue forming the stapled edge 320 of the gastric sleeve 300, and the reinforced adhesive material 108 may adhere the crimpable surgical clip 100 to the staples 350 and/or the stomach tissue.

Still referring to FIGS. 3a and 3b, in one embodiment, spring memory surgical clip 200 may generally be installed in a manner similar to the crimpable surgical clip 100. In particular, the arms 204 of spring memory surgical clip 200 may be forced open against the bias of the spring force to a disengaged position while being oriented for installation along a stapled edge 320 of a gastric sleeve 300 to fasten open edges 302 of stomach tissue together in accordance with one embodiment of the present disclosure. Similar to the configuration of the crimpable surgical clip 100 depicted in FIG. 3a, curved backbone 202 may be positioned around the open edges 302 of remaining stomach tissue such that the arms 204 extend over one or more rows of surgical staples 350.

In an embodiment, when the spring memory surgical clip 200 is oriented in the appropriate position for installation, the arms 204 may then be released to move to the engaged or closed position similar to the configuration of the crimpable surgical clip 100 depicted in FIG. 3b. In the engaged position, the grippable prongs 206 may extend into the stomach tissue forming the stapled edge 320 of the gastric sleeve 300, and the reinforced adhesive material 208 may adhere the spring memory surgical clip 200 to the staples 350 and/or the stomach tissue in accordance with one embodiment of the present disclosure.

Figure 4:
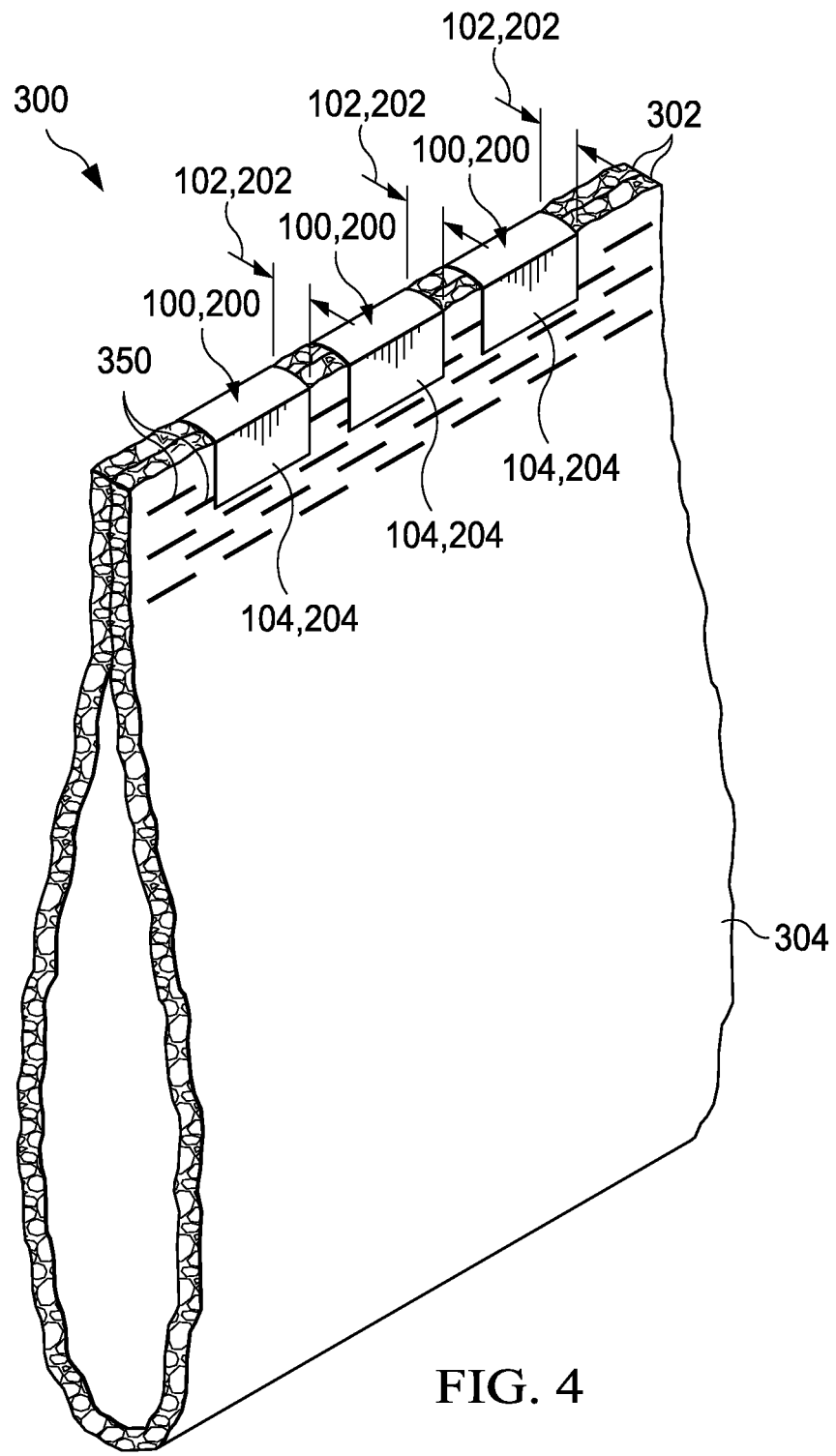
FIG. 4 is an exemplary illustration of a gastric sleeve with a plurality of surgical clips installed in accordance with one embodiment of the present disclosure.

FIG. 4 is an exemplary illustration of an entire gastric sleeve 300 with surgical clips, such as surgical clips 100, 200 of FIG. 1 and FIG. 2, for example, employed to fasten open edges 302 of stomach tissue together in accordance with one embodiment of the present disclosure.

As shown in FIG. 4, surgical clips 100, 200 are installed in the engaged position such that curved backbone 102, 202 encloses the open edges 302 of the stomach tissue and arms 104, 204 extend substantially perpendicular to the backbone 102, 202 to cover several rows of surgical staples 350. The surgical clips 100, 200 reinforce the closure formed by the stapled edge 320 of the gastric sleeve 300 to fasten the gastric sleeve 300.

In an embodiment, the quantity of surgical clips 100, 200, and the dimensions of surgical clips 100, 200, are selected to provide sufficient coverage of the open edge 302 of stomach tissue to inhibit the development of holes and gaps along the stapled edge 320 of the gastric sleeve 300 and substantially prevent leakage of gastric fluid from the gastric sleeve 300 into the abdominal cavity.

In various embodiments, the surgical clips 100, 200 may be positioned in a side-by-side orientation across the open edges 302 of the stomach tissue, or the surgical clips 100, 200 may be spaced apart by a distance ranging from about 0 mm to about 4 mm.

In an embodiment, where a plurality of rows of surgical staples 350 forms the stapled edge 320 of gastric sleeve 300, the arms 104, 204 of surgical clips 100, 200 may extend to a depth (d) covering at least three rows of staples 350.

FIG. 5a is an exemplary illustration of a surgical clip applier 500 that may be used during laparoscopic gastric sleeve surgery to deploy the crimpable surgical clip 100 of FIG. 1 to the engaged position shown in FIG. 3b and FIG. 4 to fasten the gastric sleeve 300 in accordance with one embodiment of the present disclosure. FIG. 5b is an enlarged view of the clip delivery end 510 of the surgical clip applier 500.

In one embodiment, the surgical clip applier 500 comprises an applier handle 502 with an applier actuator 504, a trocar 506, a clip delivery end 510 having a stationary axis 512, and jaws 508. During surgery, the surgeon inserts the jaws 508, the clip delivery end 510 and at least part of the trocar 506 through a laparoscopic port into the abdominal cavity of a patient's body to install the surgical clip 100. Crimpable surgical clips 100 are loaded through the applier handle 502 into the trocar 506, and a single surgical clip 100 is conveyed through the stationary axis 512 of the clip delivery end 510 to the jaws 508. The surgeon may then orient the surgical clip 100 to a position substantially perpendicular to the open edges 302 of the stapled edge 320 of the gastric sleeve 300 for installation by articulating the entire surgical clip applier 500 to the appropriate orientation. Once the disengaged surgical clip 100 is properly oriented, the surgeon may then pull the applier actuator 504 to cause the jaws 508 to apply an inward, closing force against the surgical clip 100. The jaws thereby crimp the surgical clip 100 into the engaged position shown in FIG. 3b and FIG. 4. Then the jaws 508 open again for loading of another surgical clip 100.

A similar surgical clip applier may be used to deploy the spring memory surgical clip 200 of FIG. 2 in accordance with one embodiment of the present disclosure. In an embodiment, the jaws of such a surgical clip applier would be configured to initially force the arms 204 of the spring memory surgical clip 200 apart.

The surgeon may then position the surgical clip 200 substantially perpendicular to the open edges 302 of the stapled edge 320 of the gastric sleeve 300 for installation by articulating the entire surgical clip applier to the appropriate orientation. Once the surgical clip 200 is properly oriented, the surgeon may then pull the applier actuator 504 to cause the jaws 508 to release the arms 204 of the surgical clip 100. Once released, the arms 204 of the surgical clip 200 will respond to the spring memory force by closing to the engaged position shown in FIG. 4.

FIG. 6a is an exemplary illustration of a surgical clip applier 600 that may be used during laparoscopic gastric sleeve surgery to deploy the crimpable surgical clip 100 of FIG. 1 to the engaged position shown in FIG. 3b and FIG. 4 to fasten the gastric sleeve 300 in accordance with one embodiment of the present disclosure. FIG. 6b is an enlarged view of the clip delivery end 610 of the surgical clip applier 600.

In one embodiment, surgical clip applier 600 could generally be similar to surgical clip applier 500 shown in and described in conjunction with FIGS. 5a and 5b above (with like parts having similar numbers), except that surgical clip applier 600 comprises a rotatable axis 612 on the clip delivery end 610. As such, surgical clip applier 600 comprises an applier handle 602 with an applier actuator 604, a trocar 606, a clip delivery end 610 having a rotatable axis 512, and jaws 608.

During surgery, the surgeon inserts the jaws 608, the clip delivery end 610 and at least part of the trocar 606 through a laparoscopic port into the abdominal cavity of a patient's body to install the surgical clip 100. Crimpable surgical clips 100 are loaded through the applier handle 602 into the trocar 606, and a single clip 100 is conveyed through the clip delivery end 610 to the jaws 608. During loading of surgical clip 100 into jaws 608, the rotatable axis 612 is aligned with the trocar 606.

In various embodiments, the surgeon may position the surgical clip 100 substantially perpendicular to the open edges 302 of the stapled edge 320 of the gastric sleeve 300 for installation by articulating the entire surgical clip applier 600 to the appropriate orientation with the rotatable axis 612 aligned with the trocar 606. Alternatively, or in combination with articulating the entire surgical clip applier 600, the surgeon may engage controls on the applier actuator 604 to articulate the rotatable axis 612 of the clip delivery end 610 to the desired orientation. Once the disengaged surgical clip 100 is properly oriented, the surgeon may pull the applier actuator 604 to cause the jaws 608 to apply an inward, closing force against the surgical clip 100. The jaws 608 thereby crimp the surgical clip 100 into the engaged position shown in FIG. 3b and FIG. 4 before the jaws 608 open again and the rotatable axis 612 is aligned with the trocar 606 for loading of another surgical clip 100.

A similar surgical clip applier may be used to deploy the spring memory surgical clip 200 of FIG. 2 in accordance with one embodiment of the present disclosure. In an embodiment, the jaws of such a surgical clip applier would be configured to initially force the arms 204 of the spring memory surgical clip 200 apart.

The surgeon may then position the surgical clip 200 substantially perpendicular to the open edges 302 of the stapled edge 320 of the gastric sleeve 300 for installation by articulating the entire surgical clip applier 600 to the appropriate orientation with the rotatable axis 612 aligned with the trocar 606. Alternatively, or in combination with articulating the entire surgical clip applier 600, the surgeon may engage controls on the applier actuator 604 to articulate the rotatable axis 612 of the clip delivery end 610 to the desired orientation.

Once the surgical clip 200 is properly oriented, the surgeon may then pull the applier actuator 604, thereby causing the jaws 608 to release the arms 204 of the surgical clip 200. Once released, the arms 204 of the surgical clip 200 will respond to the spring memory force by closing to the engaged position shown in FIG. 4.

It may be advantageous to set forth definitions of certain words and phrases used in this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A surgical clip comprising:
   a curved backbone having a lower side;
   a plurality of arms coupled to the curved backbone and extending perpendicular therefrom in the same direction, each arm having a facing side;
   an interior surface comprising the lower side of the curved backbone and the facing sides of the plurality of arms;
   a plurality of grippable prongs disposed along the facing sides of the plurality of arms on the interior surface; and
   wherein each of the plurality of arms is spring loaded and biased in a closed position.

2. The surgical clip of claim 1, further comprising reinforced adhesive material disposed along the interior surface.

3. A method of installing the surgical clip of claim 1, the method comprising: providing the surgical clip of claim 1
   forcing open the spring loaded arms;
   positioning the surgical clip along a stapled edge of body tissue; and
   releasing the spring loaded arms to engage and secure the stapled edge of body tissue.

4. The method of claim 3, further comprising:
   gripping the body tissue forming the stapled edge with the grippable prongs disposed along the interior surface of the surgical clip.

5. A system for installing the surgical clip of claim 1, the system comprising the surgical clip of claim 1 and a tool comprising:
   a clip delivery end to carry and position the surgical clip; and
   an actuator to cause the surgical clip to engage and secure the stapled edge of body tissue; wherein the actuator releases the clip to a closed position.

6. The system of claim 5, wherein the actuator causes the clip to be crimped.

7. The system of claim 5, further comprising:
   a handle;
   a trocar coupled to the handle and coupled to the clip delivery end; and
   jaws coupled to the clip delivery end; wherein a plurality of surgical clips are loaded through the handle into the trocar, and a surgical clip is conveyed through the clip delivery end to the jaws.

8. The system of claim 7, wherein the clip delivery end has a stationary axis.

9. The system of claim 7, wherein the clip delivery end has a rotatable axis.

10. A method of installing a surgical clip, the method comprising:
    fastening body tissue with surgical staples to form a stapled edge; and
    fastening the surgical clip across the stapled edge to inhibit the development of openings along the stapled edge, the surgical clip comprising:
    a curved backbone having a lower side;

a plurality of arms coupled to the curved backbone and extending therefrom in the same direction, each arm having a facing side; and an interior surface comprising the lower side of the curved backbone and the facing sides of the plurality of arms wherein the surgical clip is positioned perpendicular to the stapled edge.

11. The method of claim 10, further comprising:

positioning the curved backbone around open edges of body tissue along the stapled edge before fastening the surgical clip across the stapled edge.

12. The method of claim 11, further comprising:

extending the plurality of arms over one or more rows of surgical staples forming the stapled edge before fastening the surgical clip across the stapled edge.

13. The method of claim 10, further comprising gripping the body tissue forming the stapled edge with grippable prongs disposed along an interior surface of the surgical clip.

14. The method of claim 10, further comprising adhering the surgical clip to the stapled edge.

15. The method of claim 10, the method further comprising:

engaging the stapled edge of body tissue with the plurality of arms; and crimping the surgical clip to secure the stapled edge of body tissue.

16. The method of claim 15, further comprising:

gripping the body tissue forming the stapled edge with grippable prongs disposed along an interior surface of the surgical clip.

* * * * *